US009730618B2

(12) United States Patent
Beck et al.

(10) Patent No.: US 9,730,618 B2
(45) Date of Patent: Aug. 15, 2017

(54) KINETICS OF PHYSIOLOGICAL RESPONSE TO ACTIVITY DURING ACTIVITIES OF DAILY LIVING

(75) Inventors: Kenneth C. Beck, St. Paul, MN (US); Lemont Baker, Raleigh, NC (US); Kassity Yefei Liu, Sugar Land, TX (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1039 days.

(21) Appl. No.: 13/024,720

(22) Filed: Feb. 10, 2011

(65) Prior Publication Data

US 2011/0201943 A1    Aug. 18, 2011

Related U.S. Application Data

(60) Provisional application No. 61/304,908, filed on Feb. 16, 2010.

(51) Int. Cl.
| | | |
|---|---|---|
| A61B 5/02 | (2006.01) | |
| A61B 5/11 | (2006.01) | |
| G06F 19/00 | (2011.01) | |
| A61B 5/0245 | (2006.01) | |
| A61B 5/08 | (2006.01) | |

(52) U.S. Cl.
CPC ........ *A61B 5/1118* (2013.01); *G06F 19/3437* (2013.01); *A61B 5/0245* (2013.01); *A61B 5/0816* (2013.01)

(58) Field of Classification Search
CPC ......... A61B 5/0816; A61B 5/02; A61B 5/024; A61B 8/02
USPC ................ 600/301, 481, 483, 484, 486, 529
See application file for complete search history.

(56) References Cited

U.S. PATENT DOCUMENTS

| | | | |
|---|---|---|---|
| 5,431,172 | A | 7/1995 | Hoegnelid et al. |
| 5,931,858 | A | 8/1999 | Kadhiresan et al. |
| 6,045,513 | A | 4/2000 | Stone et al. |
| 6,102,874 | A | 8/2000 | Stone et al. |
| 6,190,324 | B1 | 2/2001 | Kieval et al. |
| 6,280,409 | B1 | 8/2001 | Stone et al. |

(Continued)

FOREIGN PATENT DOCUMENTS

| | | |
|---|---|---|
| AU | 2011218318 B2 | 3/2014 |
| EP | 0702980 B1 | 3/2005 |

(Continued)

OTHER PUBLICATIONS

Arena, R., et al., "Prognostic value of heart rate recovery in patients with heart failure.", Am Heart J., 151(4), (Apr. 2006), 851.e7-13.

(Continued)

*Primary Examiner* — Jacqueline Cheng
*Assistant Examiner* — Puya Agahi
(74) *Attorney, Agent, or Firm* — Schwegman Lundberg & Woessner, P.A.

(57) ABSTRACT

A physiological response to activity (PRA) during a subject's activities of daily living (ADL) can be used, such as to generate useful diagnostic information about the subject. This can involve using a template, such as an impulse response template. The technique can be used with an implantable or other ambulatory medical monitoring or therapy device, such as a cardiac function management device, or with a local or remote external interface device.

19 Claims, 2 Drawing Sheets

(56) References Cited

U.S. PATENT DOCUMENTS

| | | | |
|---|---|---|---|
| 6,371,922 B1 | 4/2002 | Baumann et al. | |
| 6,438,408 B1 | 8/2002 | Mulligan et al. | |
| 6,459,929 B1 | 10/2002 | Hopper et al. | |
| 6,490,485 B1 | 12/2002 | Sun et al. | |
| 6,539,249 B1 | 3/2003 | Kadhiresan et al. | |
| 6,572,557 B2 | 6/2003 | Tchou et al. | |
| 6,645,153 B2 | 11/2003 | Kroll et al. | |
| 6,648,830 B2 | 11/2003 | Starobin et al. | |
| 6,741,885 B1 | 5/2004 | Park et al. | |
| 6,768,919 B2 | 7/2004 | Starobin et al. | |
| 6,904,313 B1 | 6/2005 | Snell | |
| 6,961,615 B2 | 11/2005 | Kroll et al. | |
| 7,031,766 B1 | 4/2006 | Paris | |
| 7,043,294 B1 | 5/2006 | Paris | |
| 7,104,961 B2 | 9/2006 | Starobin et al. | |
| 7,171,271 B2 | 1/2007 | Koh et al. | |
| 7,177,684 B1 | 2/2007 | Kroll et al. | |
| 7,194,305 B1 | 3/2007 | Salo et al. | |
| 7,269,458 B2 | 9/2007 | Kadhiresan et al. | |
| 7,599,741 B2 | 10/2009 | Hopper et al. | |
| 7,869,877 B2 | 1/2011 | Kadhiresan et al. | |
| 2001/0037067 A1 | 11/2001 | Tchou et al. | |
| 2002/0091415 A1 | 7/2002 | Lovett et al. | |
| 2004/0073093 A1 | 4/2004 | Hatlestad | |
| 2005/0038327 A1 | 2/2005 | Tanaka et al. | |
| 2005/0090719 A1 | 4/2005 | Scheiner et al. | |
| 2005/0107723 A1 | 5/2005 | Wehman et al. | |
| 2006/0030892 A1 | 2/2006 | Kadhiresan et al. | |
| 2006/0036290 A1 | 2/2006 | Hopper et al. | |
| 2006/0293604 A1 | 12/2006 | Carlson et al. | |
| 2007/0073350 A1 | 3/2007 | Casset | |
| 2007/0161912 A1 | 7/2007 | Zhang | |
| 2008/0004668 A1* | 1/2008 | Kadhiresan et al. | 607/19 |
| 2008/0161657 A1* | 7/2008 | Bullens et al. | 600/301 |
| 2008/0249586 A1 | 10/2008 | Hopper et al. | |

FOREIGN PATENT DOCUMENTS

| | | |
|---|---|---|
| JP | 06-169903 A | 6/1994 |
| JP | 10-80408 A | 3/1998 |
| JP | 2000-51157 A | 2/2000 |
| JP | 2002-514464 A | 5/2002 |
| JP | 2006-61416 A | 3/2006 |
| WO | WO-01/23040 A1 | 4/2001 |
| WO | WO 03/096892 A1 | 11/2003 |
| WO | WO-2008/085923 A1 | 7/2008 |
| WO | WO-2011/103020 A1 | 8/2011 |

OTHER PUBLICATIONS

Fukuoka, Yoshiyuki, et al., "Dynamics of the heart rate response to sinusoidal work in humans: influence of physical activity and age", Clinical Science, 102, (2002), 31-38.

Miyamoto, Yoshimi, et al., "Cardiorespiratory Dynamics during Sinusoidal and Impulse Exercise in Man", Japanese Journal of Physiology, vol. 33, No. 6, (1983), 971-986.

Sato, Iwao, et al., "System analysis of heart rate control in man", Journal of Applied Physiology, vol. 41, No. 5, (Nov. 1976), 790-796.

Schalcher, C., et al., "Prolonged oxygen uptake kinetics during low-intensity exercise are related to poor prognosis in patients with mild-to-moderate congestive heart failure.", Chest, 124(2), (Aug. 2003), 580-6.

Shetler, K., et al., "Heart rate recovery: validation and methodologic issues", J Am Coll Cardiol., 38(7), (Dec. 2001), 1980-7.

Stremel, R. W., et al., "Modeling Static and Dynamic Human Cardiovascular Responses to Exercise", Computer Programs in Biomedicine 4, (1975), 246-252.

Buller, N. P., et al., "Mechanism of the increased ventilatory response to exercise in patients with chronic heart failure", British Heart Journal, 63(5), (May 1990), 281-283.

Francis, D. P., et al., "Cardiopulmonary exercise testing for prognosis in chronic heart failure continuous and independent prognostic value from VE/VCO$_2$slope and peak VO$_2$", Eur Heart J., 21(2), (Jan. 2000), 154-161.

Keteyian, S. J., et al., "Effects of exercise training on chronotropic incompetence in patients with heart failure", American Heart Journal, 138(2 Pt 1), (Aug. 1999), 233-40.

Sullivan, M. J., "Relation between central and peripheral hemodynamics during exercise in patients with chronic heart failure Muscle blood flow is reduced with maintenance of arterial perfusion pressure", Circulation, 80(4), (Oct. 1989), 769-781.

"International Application Serial No. PCT/US2011/024325, International Preliminary Report on Patentability mailed Aug. 30, 2012", 9 pgs.

"International Application Serial No. PCT/US2011/024325, International Search Report mailed Jul. 18, 2011", 4 pgs.

"International Application Serial No. PCT/US2011/024325, Written Opinion mailed Jul. 18, 2011", 9 pgs.

Boehmer, J. P, et al., "Implantable Sensors Measure Physiologic Response to Activity during Activities of Daily Living", (Abstract Only), 15th Annual Scientific Meeting of the Heart Failure Society of America, Sep. 18-21, 2011, Boston, MA, (2011), 2 pgs.

Boehmer, J. P, et al., "Implantable Sensors Measure Physiologic Response to Activity during Activities of Daily Living", 15th Annual Scientific Meeting of the Heart Failure Society of America, Sep. 18-21, 2011, Boston, MA, (2011), 1 pg.

Boehmer, J. P., et al., "Physiologic Sensor Response to Activity Level in the MultiSENSE Study", (Abstract 340), Journal of Cardiac Failure, 17(8),(Supplement), (Aug. 2011), S105-S106.

Page, E., et al., "Physiological approach to monitor patients in cogestive heart failure: application of a new implantable device-based system to monitor daily life activity and ventilation", Europace vol. 9 No. 8, (Jan. 1, 2007), 687-693.

Wilkoff, B. L., et al., "A Mathematical Model of the Cardiac Chronotropic Response to Exercise", Journal of Electropphysiology, 3(3), (1989), 176-180.

"U.S. Appl. No. 11/184,327, Non Final Office Action mailed Feb. 10, 2014", 9 pgs.

"Australian Application Serial No. 2011218318, First Examiner Report mailed Jul. 12, 2013", 2 pgs.

"Australian Application Serial No. 2011218318, Response filed Feb. 4, 2014 to First Examiner Report mailed Jul. 12, 2013", 3 pgs.

"Japanese Application Serial No. 2008-522809, Office Action mailed Jul. 22, 2013", With English Translation, 8 pgs.

"Japanese Application Serial No. 2008-522809, Response filed Oct. 9, 2012 to Office Action mailed Apr. 9, 2012", (w/ English Translation of Claims), 16 pgs.

"Japanese Application Serial No. 2012-552990, Office Action mailed Dec. 17, 2013", With English Translation, 3 pgs.

"U.S. Appl. No. 11/184,327, Examiner Interview Summary mailed Jun. 2, 2014", 3 pgs.

"U.S. Appl. No. 11/184,327, Final Office Action mailed Sep. 12, 2014", 7 pgs.

"U.S. Appl. No. 11/184,327, Response filed May 27, 2014 to Non Final Office Action mailed Feb. 10, 2014", 9 pgs.

"U.S. Appl. No. 11/184,327, Appeal Brief filed Feb. 4, 2015", 28 pgs.

"U.S. Appl. No. 11/184,327, Examiner Interview Summary mailed Sep. 30, 2014", 3 pgs.

"U.S. Appl. No. 11/184,327, Examiner Interview Summary mailed Oct. 14, 2014", 3 pgs.

"European Application Serial No. 06786721.8, Examination Notification Art. 94(3) mailed Nov. 14, 2014", 6 pgs.

* cited by examiner

KINETICS OF PHYSIOLOGICAL RESPONSE TO ACTIVITY DURING ACTIVITIES OF DAILY LIVING

CROSS-REFERENCE TO RELATED APPLICATIONS

This application claims the benefit of U.S. Provisional Application No. 61/304,908, filed on Feb. 16, 2010, under 35 U.S.C. §119(e), which is incorporated herein by reference in its entirety.

BACKGROUND

Congestive heart failure (CHF) is a condition in which blood circulation provided by the heart is impaired. CHF is a common, disabling, and costly condition. CHF can be treated by drug therapy and, sometimes, by implantable cardiac function management devices, such as for providing cardiac resynchronization therapy (CRT). A patient's chronic stable heart failure may abruptly decompensate, requiring hospitalization. Therefore, monitoring a patient's cardiac status, such as for CHF, can help avoid such acute decompensation and hospitalization.

OVERVIEW

The present inventors have recognized, among other things, a need for improved diagnostic indicators, such as for diagnosing CHF status, for example. This document describes, among other things, how a physiological response to activity (PRA) during a subject's activities of daily living (ADL) can be used, such as to generate useful diagnostic information about the subject.

Patients with CHF exhibit slowed kinetics of physiological responses to activity. This can be demonstrated in a laboratory setting, such as by having a patient first maintain a low level of physical activity, until physiological processes become reasonably steady over time. Then, if an abrupt increase in activity is imposed, such as by placing the patient on a treadmill, for example, physiological responses such as heart rate, contractility, stroke volume, or respiratory activity (e.g., tidal volume, respiratory rate, or their product, i.e., minute ventilation) will respond relatively slowly in a CHF patient, as compared a person without CHF. The slowed kinetics of PRA is related to the reduced cardiac function of the CHF patient. However, this test is difficult to administer. It is believed that the slowed kinetics of physiological responses to changes in activity will be roughly proportional to the severity of cardiac limitation. The slowed kinetics may contribute to patient symptoms, such as shortness of breath, exercise limitation, or fatigue. This document describes, among other things, systems and methods for determining the kinetic response of physiological processes to changes in activity by continuously monitoring both activity and physiological responses during a patient's normal activities of daily living. As described in detail below, this can involve using a template, such as an impulse response template, such as to determine response kinetics.

Example 1 describes subject matter that can include an apparatus. The apparatus can comprise an activity sensor circuit, configured to receive an activity signal indicative of physical activity of a subject during the subject's activities of daily living. A physiological sensor circuit can be included, and configured to receive a concurrent actual physiological response signal, different from the activity signal, during the subject's activities of daily living. A signal processor circuit can be included, and configured to generate an approximate physiological response signal, including convolving the activity signal with a template for generating the approximate physiological response signal, the template including at least one characteristic parameter, and comparing information from the approximate physiological response signal with information from the actual physiological response signal to determine the at least one characteristic parameter. The signal processor circuit can be configured to provide information from the at least one characteristic parameter to a user or process.

In Example 2, the subject matter of Example 1 can optionally include an activity sensor circuit that includes an accelerometer configured to receive the activity signal including an acceleration signal, and wherein receiving the concurrent actual physiological response signal includes receiving at least one of a heart rate or interval signal or a respiration signal.

In Example 3, the subject matter of any one of Examples 1-2 can optionally include the signal processor circuit being configured to generate the approximate physiological response signal including iteratively generating the approximate physiological response signal so as to reduce or minimize a difference between the approximate physiological response signal and the actual physiological response signal.

In Example 4, the subject matter of any one of Examples 1-3 can optionally include the signal processor circuit that includes a time-to-frequency domain transform circuit, and wherein the signal processor circuit is configured to convolve the activity signal with a template including multiplying a frequency domain representation of the activity signal with a frequency domain representation of the impulse response template.

In Example 5, the subject matter of any one of Examples 1-4 can optionally include the signal processor circuit is configured to convolve the activity signal with a template, including convolving the activity signal with an impulse response template.

In Example 6, the subject matter of any one of Examples 1-5 can optionally include the signal processor circuit being configured to convolve the activity signal with a template including using a time-domain impulse response template that includes an exponential function of time, and wherein the at least one characteristic parameter includes at least one of a scaling constant of the exponential function or a time constant of the exponential function.

In Example 7, the subject matter of any one of Examples 1-6 can optionally include the signal processor circuit being configured to trend the at least one characteristic parameter over time, and is configured to provide a diagnostic of the subject using the trended characteristic parameter.

In Example 8, the subject matter of any one of Examples 1-7 can optionally include at least one characteristic parameter that includes the time constant, and the signal processor circuit can be configured to provide the diagnostic indicating worsening of cardiac status when the trended time constant increases over time.

In Example 9, the subject matter of any one of Examples 1-8 can optionally include at least one characteristic parameter includes the scaling constant, and the signal processor circuit can be configured to provide the diagnostic indicating worsening of chronotropic incompetence when the trended scaling constant decreases over time.

In Example 10, the subject matter of any one of Examples 1-9 can optionally include at least one characteristic parameter includes the scaling constant, and the signal processor circuit can be configured to provide the diagnostic indicating a worsening of cardiac status when the trended scaling constant increases over time.

Example 11 can include, or can optionally be combined with any one of Examples 1-10 to include, a device-readable medium. The device-readable medium can include instructions that, when performed by the device, can comprise: receiving an activity signal indicative of physical activity of a subject during the subject's activities of daily living; receiving a concurrent actual physiological response signal, different from the activity signal, during the subject's activities of daily living; generating an approximate physiological response signal, including: convolving the activity signal with a template for generating the approximate physiological response signal, the template including at least one characteristic parameter; and comparing information from the approximate physiological response signal with information from the actual physiological response signal to determine the at least one characteristic parameter; and providing information from the at least one characteristic parameter to a user or process.

In Example, 12 the subject matter of any one of Examples 1-11 can optionally be configured or performed such that receiving the activity signal includes receiving an acceleration signal, and wherein receiving the concurrent actual physiological response signal includes receiving at least one of a heart rate or interval signal or a respiration signal.

In Example 13, the subject matter of any one of Examples 1-12 can optionally be configured or performed such that generating the approximate physiological response signal includes iteratively generating the approximate physiological response signal so as to reduce or minimize a difference between the approximate physiological response signal and the actual physiological response signal.

In Example 14, the subject matter of any one of Examples 1-13 can optionally be configured or performed such that convolving the activity signal with a template includes multiplying a frequency domain representation of the activity signal with a frequency domain representation of the impulse response template.

In Example 15, the subject matter of any one of Examples 1-14 can optionally be configured or performed such that convolving the activity signal with a template includes convolving the activity signal with an impulse response template.

In Example 16, the subject matter of any one of Examples 1-15 can optionally be configured or performed such that convolving the activity signal with a template includes using a time-domain impulse response template that includes an exponential function of time, and wherein the at least one characteristic parameter includes at least one of a scaling constant of the exponential function or a time constant of the exponential function.

In Example 17, the subject matter of any one of Examples 1-16 can optionally comprise trending the at least one characteristic parameter over time, and providing a diagnostic of the subject using the trended characteristic parameter.

In Example 18, the subject matter of any one of Examples 1-17 can optionally be configured or performed such that the at least one characteristic parameter includes the time constant, and the diagnostic can be configured to indicate worsening of cardiac status when the trended time constant increases over time.

In Example 19, the subject matter of any one of Examples 1-18 can optionally be configured or performed such that the at least one characteristic parameter includes the scaling constant, and the diagnostic can be configured to indicate worsening of chronotropic incompetence when the trended scaling constant decreases over time.

In Example 20, the subject matter of any one of Examples 1-19 can optionally be configured or performed such that the at least one characteristic parameter includes the scaling constant, and the diagnostic can be configured to indicate a worsening of cardiac status when the trended scaling constant increases over time.

These examples can be combined in any permutation or combination. This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
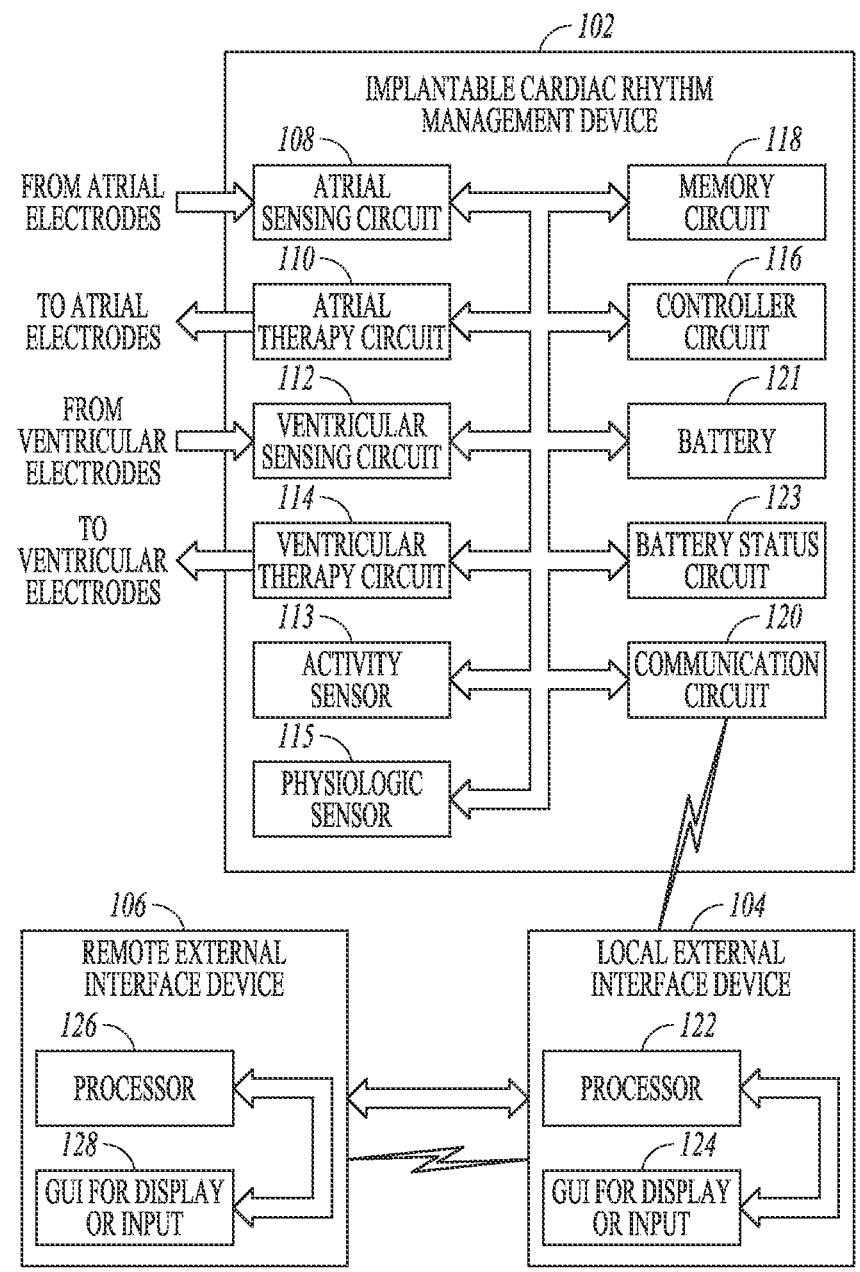
FIG. 1 shows an example of portions of a cardiac function management system and an environment in which it is used.

FIG. 1 shows an example of portions of a cardiac function management system 100 and an environment in which it is used. In an example, the system 100 can include an ambulatory medical device, such as an external (e.g., wearable) medical device or an implantable cardiac rhythm or function management device 102, a local external interface device 104, and an optional remote external interface device 106.

In an example, the implantable device 102 can include an atrial sensing circuit 108, an atrial therapy circuit 110, a ventricular sensing circuit 112, a ventricular therapy circuit 114, a controller circuit 116, a memory circuit 118, a communication circuit 120, a power source such as a battery 121, a battery status circuit 123, an activity sensor 113 configured to sense a physical activity signal of a patient or other subject, and a physiologic sensor 115 configured to sense a physiologic signal, different from the physical activity signal, of the subject.

In an example, the atrial sensing circuit 108 can be coupled to electrodes, such as an intra-atrial electrode or any other electrode that permits sensing of an intrinsic atrial cardiac signal including atrial depolarization information. The atrial therapy circuit 110 can similarly be coupled to these or other electrodes, such as for delivering pacing, cardiac resynchronization therapy (CRT), cardiac contractility modulation (CCM) therapy, defibrillation/cardioversion shocks, or other energy pulses to one or both atria.

In an example, the ventricular sensing circuit 112 can be coupled to electrodes, such as an intra-ventricular electrode or any other electrode that permits sensing of an intrinsic ventricular cardiac signal including ventricular depolarization information. The ventricular therapy circuit 114 can similarly be coupled to these or other electrodes, such as for delivering pacing, cardiac resynchronization therapy (CRT), cardiac contractility modulation (CCM) therapy, defibrillation/cardioversion shocks, or other energy pulses to one or both ventricles.

In an example, the activity sensor 113 can include a single or multiple axis accelerometer, such as to sense an acceleration of the subject that is indicative of physical activity of the subject. The activity sensor 113 can also include a sensor interface circuit, configured to process the acceleration signal and provide a resulting physical activity signal. In an example, the physical activity signal can be indicative of a physical exertion of the subject. In an example, the activity sensor 113 can also be used for other purposes, such as to sense the subject's posture, heart sounds, or other information available from an acceleration signal.

In an example, the physiologic sensor 115 can include a respiration sensor, such as an impedance or other sensor, which can include electrodes configured to deliver a test energy, such as to the subject's thorax, and to sense a responsive voltage signal, such as indicative of the thoracic impedance, and which can be filtered to provide information about respiration, heart contraction, or thoracic fluid accumulation.

A controller circuit 116 can be coupled to the atrial sensing circuit 108 and the ventricular sensing circuit 112, such as to receive information from the sensed cardiac signals. The controller circuit 116 can also be coupled to the activity sensor 113 to receive information about the subject's physical activity or exertion level. The controller circuit 116 can also be coupled to the physiologic sensor 115, such as to receive other physiologic information. In an example, such other physiologic information can include cardiac contraction signal, such as to provide information about the subject's heart rate or interval, stroke volume, or other information available from the cardiac contraction signal. In an example, the other physiologic information can include a respiration signal, such as to provide information about the subject's breathing rate or interval, tidal volume, or other information available from the respiration signal. In an example, the controller circuit 116 can include a signal processor circuit, such as a digital signal processor (DSP) circuit, such as for extracting a template parameter from which a diagnostic indicator can be generated, as described below. In an example, the signal processor circuit can include dedicated circuitry for performing one or more signal processing functions, such as convolution in the time-domain or the frequency domain, or signal conversion from the time-domain to the frequency-domain or from the frequency domain to the time-domain.

In an example, the controller circuit 116 can be coupled to the atrial therapy circuit 110 and the ventricular therapy circuit 114 to provide control or triggering signals to trigger timed delivery of the therapy pulses. In an example, the controller circuit 116 can be configured to provide control to help permit the CCM therapy to be effectively delivered, such as in combination with one or more other therapies (e.g., bradycardia pacing, antitachyarrhythmia pacing (ATP), cardiac resynchronization therapy (CRT), atrial or ventricular defibrillation shock therapy) or functionalities (e.g., autothreshold functionality for automatically determining pacing threshold energy, autocapture functionality for automatically adjusting pacing energy to capture the heart, etc.). In an example, this can include providing dedicated modules within the controller circuit 116, or providing executable, interpretable, or otherwise performable code configure the controller circuit 116.

A memory circuit 118 is coupled to the controller circuit 116, such as to store control parameter values, physiological data, or other information. A communication circuit 120 is coupled to the controller circuit 116 to permit radiofrequency (RF) or other wireless communication with an external device, such as the local external interface device 104 or the remote external interface device 106.

In an example, the battery 121 can include one or more batteries to provide power for the implantable device 102. In an example, the battery 121 can be rechargeable, such as by wireless transcutaneous power transmission from an external device to the implantable device 102. The battery status circuit 123 can be communicatively coupled to each of the battery 121 and the controller circuit 116, such as to determine battery status information, for example, indicative of how much energy remains stored in the battery 121. The controller circuit 116 can be configured to alter operation of the implantable device 102, such as based at least in part on the battery status information.

In an example, the local external interface device 104 can include a processor 122 and a graphic user interface (GUI) 124 or like device for displaying information or receiving user input as well as a communication circuit, such as to permit wired or wireless communication with the remote external interface device 106 over a communications or computer network. Similarly, the remote external interface device 106 can include a processor 126 and a graphic user interface (GUI) 128 or like device for displaying information or receiving user input as well as a communication circuit, such as to permit wired or wireless communication with the local external interface device 104 over the communications or computer network.

Because the system 100 includes processing capability in the ambulatory or implantable device 102 (e.g., provided by the controller circuit 116), the local external interface device 104 (e.g., provided by the processor 122), and the remote external interface device 106 (e.g., provided by the processor 126), various methods discussed in this document can be implemented at any of such locations, or tasks can be distributed between two or more of such locations.

Figure 2:
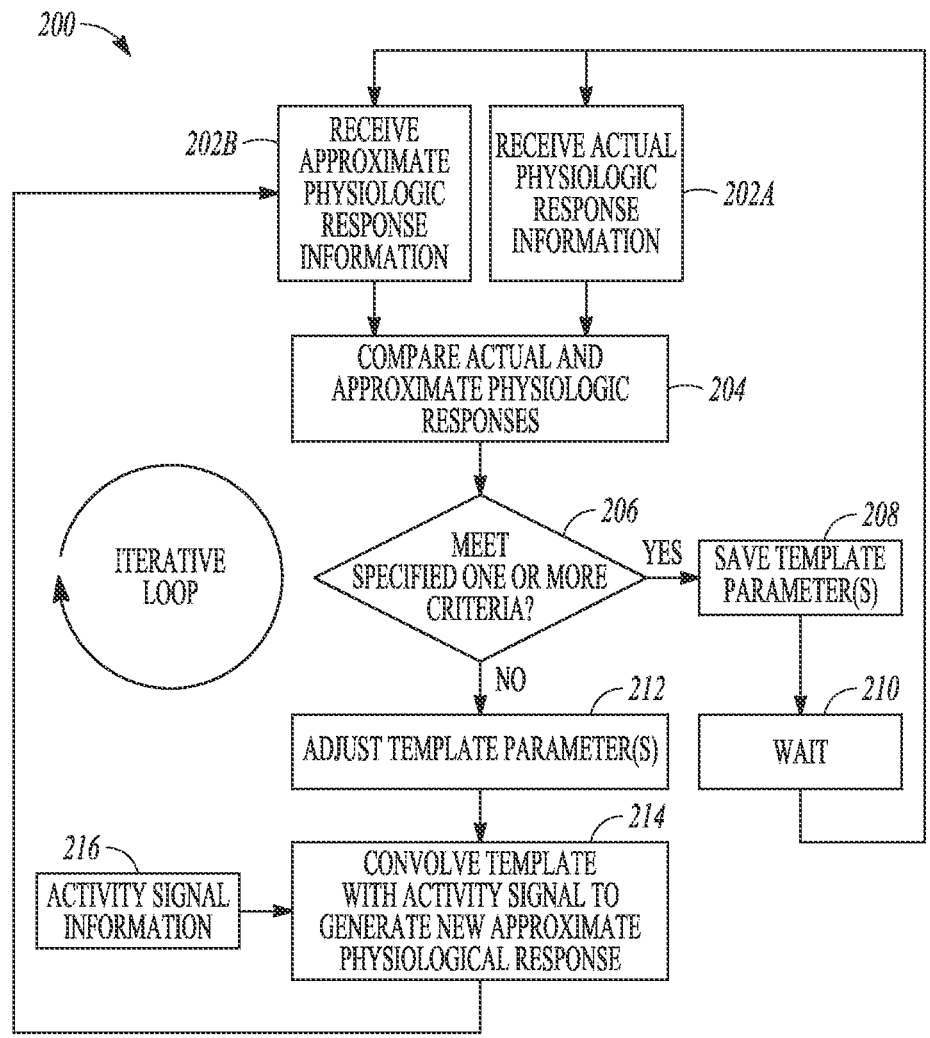
FIG. 2 shows an example of how a physiological response to activity (PRA) during a subject's activities of daily living (ADL) can be used, such as to generate useful diagnostic information about the subject.

FIG. 2 shows an example 200 of how a physiological response to activity (PRA) during a subject's activities of daily living (ADL) can be used, such as to generate useful diagnostic information about the subject. As described in detail below, this can involve using a template, such as an impulse response template that can be convolved with an activity signal. The subject's ADL involve the subject's normal everyday physical activities, such as walking, sleeping, sitting, standing, bending, exercising or the like. The present systems and methods are capable of extracting useful diagnostic information from the subject's ADL—without requiring that the subject undergo a prescribed exercise regimen (e.g., a cardiac stress test, treadmill test, or the like), which are considered outside the subject's ADL because they are prescribed activities that must be undertaken in order to extract the diagnostic information. By contrast, the present diagnostic information can be obtained without subjecting the subject to one or more prescribed activities from which the diagnostic information is extracted. Instead, the present diagnostic information can be obtained while the subject is undergoing his or her ordinary (or atypical) everyday activities, without requiring any such prescribed regimen.

Moreover, determining the subject's PRA can involve monitoring one or more physiologic signals during the subject's ADL. The physiologic signal may change during or after such ADL. In an example, such changes in the physiologic signal that accompany the variations in the subject's physical activity provided by the subject's ADL can be regarded as the subject's PRA, whether such changes in the physiologic signal are actually in response to such ADL of the subject, or merely accompany the ADL, such as during or after the ADL.

At 202A in FIG. 2, actual physiologic signal information, such as can be obtained in response to (e.g., during) the subject's activities of daily living can be obtained during a representative period of time. At 202B, an approximate physiologic signal, for the same representative period of time, can be received. (Initially, the approximate physiologic signal can be generated by first seeding a nominal set of template parameters, and performing one or more iterations of the iterative loop described below, e.g., starting at the convolution at 214, such as described below).

In an example, the actual physiologic signal can include a heart rate (HR) or interval signal. The HR signal can provide information as to how fast successive heart contractions are occurring in the subject. In an example, the actual physiologic signal can include a respiration signal. In an example, the respiration signal can include a respiration rate (RR) or interval signal. The RR signal can provide information as to how fast successive breaths are occurring in the subject. In an example, the respiration signal can include a minute ventilation (MV) signal, which can be represented as MV=TV·RR, where MV represents minute ventilation, TV represents the tidal volume (air expelled per breath), and RR represents the respiration rate indicating how fast the subject is breathing. One or more other physiologic response variables can also be used.

At 204, the actual and approximate physiologic response signals can be compared. In an example, this can include comparing the actual and approximate physiologic signals, corresponding to the same representative time period. In an example, this comparing of the actual and approximate physiologic signals can include performing a time-domain subtraction of approximate and actual data points, corresponding to the same time, squaring these differences, and summing these squared differences to yield a sum-of-squared-differences indication of the cumulative discrepancy between the approximate and actual physiologic response signals over the representative time period.

At 206, the computed indication of the discrepancy between the approximate an actual physiologic response signals over the representative time period can be compared to one or more criteria. In an example, this can include comparing the amount of the discrepancy to a specified static or dynamic minimum threshold value. In an example, this can include testing various combinations of the template parameters and selecting the combination of template parameters that yields the minimum discrepancy between the approximate and actual physiologic response signals over the representative time period. In an example, the various combinations of template parameters can be tested exhaustively. In an example, the various combinations of template parameters can be tested more sparingly, such as by using a numerical best fit search routine, such as downhill simplex or the like, or other techniques for intelligently traversing the space of the various combinations of template parameters.

At 206, if the one or more criteria are met, or the parameter combination yielding the minimum value of discrepancy between the approximate and actual physiologic response signals is established, then, at 208, the corresponding one or more parameters associated with the template can be saved and, after optionally waiting a specified period of time at 210, the process can return to 202A-B.

At 206, if the discrepancy between the approximate and actual physiologic response signals exceeds the threshold value, then the process can proceed to 212. At 212, one or more of the template parameters can be adjusted, such as in a direction that tends to reduce or minimize the discrepancy between the approximate and actual physiologic responses.

In an example, the template can include an impulse response template. In an example, the impulse response template can be approximated by a first-order exponential model. Such an impulse response template can be represented in the time domain by $h(t)=A \cdot e^{-(t/\tau)}$, where h(t) is the time domain impulse response, "A" can represent a scaling constant and "τ" can represent a characteristic time constant. The scaling constant, A, and time constant, τ, can form parameters of this first-order exponential impulse response template h(t). At 212, one or both of the scaling constant and the time constant can be adjusted, such as to reduce or minimize the discrepancy between the approximate and actual physiologic responses.

At 214, after one or both of the template parameters have been adjusted, the impulse response template can be convolved with the physical activity signal, such as can be derived from the activity sensor 113 and provided at 216, such as to generate a new approximate physiologic response signal to be iteratively compared against the actual physiologic response signal at 204 until the specified one or more criteria are met at 206 or a discrepancy between the approximate and actual physiologic response signals is minimized. In this way, 204, 206, 212, and 214 can form a loop for iteratively arriving at an approximate physiologic response signal that is as close to the actual physiologic response signal as the first-order exponential model of the impulse response template permits, or at least until the specified one or more criteria are met at 206.

In an example, the convolution of the impulse response template with the physical activity signal can be carried out using a time domain (e.g., fold-and-shift) signal convolution operation. In an example, the convolution of the impulse response template with the physical activity signal can be carried out by converting each of the impulse response template and the physical activity signal into the frequency domain, such that the convolution can be carried out by performing a multiplication of the frequency domain impulse response template by the frequency domain representation of the physical activity signal. In an example, the time-domain-to-frequency-domain conversion can be carried out using a Fast Fourier Transform (FFT) circuit that can be included in the signal processing circuit of the controller circuit 116.

At 208, the saved one or more template parameters (e.g., scaling constant or time constant) need not be immediately discarded and overwritten by new values of the template parameters. Instead, the template parameters can be stored (e.g., in a first-in-first-out (FIFO) memory buffer in the memory circuit 118) and trended over time, and used to provide diagnostic information about the subject. In an illustrative example, the optional wait at 210 can be a 24-hour wait period, and the actual physiologic response information at 202A and the approximate physiologic response information at 202B can constitute a one-day period of such information, and the template parameters saved at 208 can represent daily values that can be stored and trended over an extended period of time, such as weeks, months, or even years. The optional wait at 210 can be for shorter or longer periods. For instance, multiple periods of several minutes to several hours can be fit, such as in FIG. 2, and the parameters can be stored, such as for averaging together (to build a daily average or computing some other indication of central tendency) or for trending individually.

Table 1 shows an example of diagnostic information that the present inventors believe can be derived from one or more trended template parameters (e.g., A, τ).

TABLE 1

Diagnostic Information From Impulse Response Template Parameters

| Physiologic Signal | Change in Trended Parameter Over Time | Diagnostic Indicator |
|---|---|---|
| Heart Rate | Increased Time Constant, τ | Worsening cardiac status (e.g., worsening congestive heart failure (CHF)) |
| Minute Ventilation | Increased Time Constant, τ | Worsening cardiac status (e.g., worsening congestive heart failure (CHF)) |
| Heart Rate | Reduced Scaling Constant, A | Worsening chronotropic incompetence |
| Heart Rate | Increased Scaling Constant, A | Worsening cardiac status (e.g., worsening congestive heart failure (CHF)) |
| Minute Ventilation | Increased Scaling Constant, A | Worsening cardiac status (e.g., worsening congestive heart failure (CHF)) |

In an example, the one or more impulse response template parameters, one or more trended impulse response template parameters, or diagnostic or other information that can be derived from one or more such impulse response template parameters can be communicated from the ambulatory or implantable medical device. In an example, such information can be communicated from the implantable cardiac rhythm management device 102, such as via the communication circuit 120, to the local external interface device 104 or the remote external interface device 106, such as for textual (e.g., alphanumeric) or non-textual (e.g., non-alphanumeric) display of useful diagnostic information to a user.

ADDITIONAL NOTES

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on the objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, the code may be tangibly stored on one or more volatile or non-volatile tangible computer-readable media during execution or at other times. These computer-readable media may include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

The claimed invention is:
1. An apparatus comprising:
   an activity sensor circuit, configured to receive information indicative of physical activity of a subject during the subject's activities of daily living and to generate an activity signal;
   a physiological sensor circuit, configured to receive physiological information during the subject's activities of daily living and concurrent with the information indicative of physical activity, and to generate an actual physiological response signal different from the activity signal;

a signal processor circuit, configured to receive a template comprising a plurality of data values characterizing a relationship between the information indicative of physical activity and the physiological information, and generate an approximate physiological response signal including performing a mathematical convolution operation of the activity signal with the template, the approximate physiological response signal representative of the actual physiological response signal, wherein the signal processor circuit is further configured to:

compare information from the approximate physiological response signal, generated using the mathematical convolution, with information from the actual physiological response signal;

when the comparison fails to meet at least one specified criterion, adjust the template and generate a corresponding approximate physiological response signal including performing the mathematical convolution operation of the activity signal with the adjusted template, until the comparison meets the specified criterion;

when the comparison meets the at least one specified criterion, extract from the template at least one characteristic parameter and generate an indicator of kinetics of physiological response to a change in activity (PRA); and use information from the at least one characteristic parameter to determine a diagnostic indicating a change of cardiac status related to the kinetics of PRA; and a therapy circuit coupled to the signal processor circuit, the therapy circuit configured to deliver a therapy to the subject based at least on the determined diagnostic.

2. The apparatus of claim 1, wherein the activity sensor circuit includes an accelerometer configured to receive the activity signal including an acceleration signal, and wherein receiving the actual physiological response signal includes receiving at least one of a heart rate or interval signal or a respiration signal.

3. The apparatus of claim 1, wherein the signal processor circuit is configured to generate the approximate physiological response signal including adjusting the template, and iteratively comparing the approximate physiological response signal, generated using the adjusted template, and the actual physiological response signal.

4. The apparatus of claim 1, wherein the signal processor circuit includes a time-to-frequency domain transform circuit, and wherein the signal processor circuit is configured to convolve the activity signal with the template including multiplying a frequency domain representation of the activity signal with a frequency domain representation of an impulse response template.

5. The apparatus of claim 1, wherein the signal processor circuit is configured to convolve the activity signal with the template, including performing a mathematical convolution operation of the activity signal with an impulse response template.

6. The apparatus of claim 5, wherein the signal processor circuit is configured to convolve the activity signal with the template including using a time-domain impulse response template that includes an exponential function of time, and wherein the at least one characteristic parameter includes at least one of a scaling constant of the exponential function or a time constant of the exponential function.

7. The apparatus of claim 6, wherein the signal processor circuit is configured to trend the at least one characteristic parameter over time, and is configured to provide the diagnostic of the subject using the trended characteristic parameter.

8. The apparatus of claim 7, wherein the at least one characteristic parameter includes the time constant, and wherein the signal processor circuit is configured to provide the diagnostic indicating worsening of cardiac status when the trended time constant increases over time.

9. The apparatus of claim 7, wherein the at least one characteristic parameter includes the scaling constant, and wherein the signal processor circuit is configured to provide the diagnostic indicating worsening of chronotropic incompetence when the trended scaling constant decreases over time.

10. The apparatus of claim 7, wherein the at least one characteristic parameter includes the scaling constant, and wherein the signal processor circuit is configured to provide the diagnostic indicating a worsening of cardiac status when the trended scaling constant increases over time.

11. A non-transitory device-readable medium including instructions that, when performed by the device, comprise:

receiving information indicative of physical activity of a subject during the subject's activities of daily living and generating an activity signal;

receiving physiological information during the subject's activities of daily living and concurrent with the information indicative of physical activity and generating an actual physiological response signal, different from the activity signal;

receiving a template comprising a plurality of data values;

generating an approximate physiological response signal that is representative of the actual physiological response signal, including:

performing a mathematical convolution operation of the activity signal with the template for generating the approximate physiological response signal;

comparing information from the approximate physiological response signal, generated using the mathematical convolution, with information from the actual physiological response signal;

when the comparison fails to meet at least one specified criterion, adjusting the template and performing the mathematical convolution operation of the activity signal with the adjusted template, until the comparison meets the specified criterion; and when the comparison meets the at least one specified criterion, extracting from the template at least one characteristic parameter indicative of kinetics of physiological response to a change in activity;

using information from the at least one characteristic parameter to determine a diagnostic indicating a change of cardiac status; and delivering a therapy to the subject based at least on the determined diagnostic.

12. The non-transitory device-readable medium of claim 11, wherein receiving information indicative of physical activity of a subject includes receiving an acceleration signal, and wherein receiving physiological information during the subject's activities of daily living includes receiving at least one of a heart rate or interval signal or a respiration signal.

13. The non-transitory device-readable medium of claim 11, wherein generating the approximate physiological response signal includes adjusting the template, and iteratively comparing the approximate physiological response signal, generated using the adjusted template, and the actual physiological response signal.

14. The non-transitory device-readable medium of claim 11, wherein convolving the activity signal with the template includes multiplying a frequency domain representation of the activity signal with a frequency domain representation of an impulse response template.

15. The non-transitory device-readable medium of claim 11, wherein performing the mathematical convolution operation of the activity signal with the template includes convolving the activity signal with an impulse response template.

16. The non-transitory device-readable medium of claim 15, wherein performing the mathematical convolution operation of the activity signal with the template includes using a time-domain impulse response template that includes an exponential function of time, and wherein the at least one characteristic parameter includes at least one of a scaling constant of the exponential function or a time constant of the exponential function.

17. The non-transitory device-readable medium of claim 16, comprising trending the at least one characteristic parameter over time, and providing the diagnostic of the subject using the trended characteristic parameter.

18. The non-transitory device-readable medium of claim 17, wherein the at least one characteristic parameter includes the time constant, and wherein the diagnostic is configured to indicate worsening of cardiac status when the trended time constant increases over time.

19. The non-transitory device-readable medium of claim 17, wherein the at least one characteristic parameter includes the scaling constant, and wherein the diagnostic is configured to indicate one or more of worsening of chronotropic incompetence when the trended scaling constant decreases over time, or a worsening of cardiac status when the trended scaling constant increases over time.

* * * * *